(12) United States Patent
Buja

(10) Patent No.: US 9,615,752 B2
(45) Date of Patent: Apr. 11, 2017

(54) SYSTEM AND METHOD EMPLOYING A THERMOCOUPLE JUNCTION FOR MONITORING OF PHYSIOLOGICAL PARAMETERS

(71) Applicant: Frederick J. Buja, Rochester, NY (US)

(72) Inventor: Frederick J. Buja, Rochester, NY (US)

( * ) Notice: Subject to any disclaimer, the term of this patent is extended or adjusted under 35 U.S.C. 154(b) by 69 days.

(21) Appl. No.: 14/341,133

(22) Filed: Jul. 25, 2014

(65) Prior Publication Data

US 2015/0025331 A1    Jan. 22, 2015

Related U.S. Application Data

(63) Continuation of application No. 11/838,491, filed on Aug. 14, 2007, now Pat. No. 8,790,256.
(Continued)

(51) Int. Cl.
*A61B 5/01* (2006.01)
*A61B 5/087* (2006.01)
(Continued)

(52) U.S. Cl.
CPC .............. *A61B 5/01* (2013.01); *A61B 5/021* (2013.01); *A61B 5/026* (2013.01);
(Continued)

(58) Field of Classification Search
CPC ......... A61B 5/01; A61B 5/021; G01K 13/002
(Continued)

(56) References Cited

U.S. PATENT DOCUMENTS 3,049,012 A    8/1962  Daniels
3,314,129 A    4/1967  Pugh et al.
(Continued)

FOREIGN PATENT DOCUMENTS

CA    2274308    4/2005
CA    2427832    1/2008
(Continued)

OTHER PUBLICATIONS

Prosecution History of Related U.S. Appl. No. 11/381,246, filed May 2, 2006 (US Pub 20060246167).
(Continued)

*Primary Examiner* — Michael C Stout
(74) *Attorney, Agent, or Firm* — Duane C. Basch; Basch & Nickerson LLP

(57) ABSTRACT

Disclosed are systems and methods for enabling the acquisition of physiological parameters of a mammal or other specimen using thermo-mechanical responses (e.g., temperature, pressure and alternatively acceleration, pulse, position). In accordance with one example embodiment, a monitoring device for wired and/or wireless sensors is used to acquire a series of sensor signals that are attached to achieve the physiological measurements of a mammal vital signs is provided. The device includes a Temperature-Pressure (T-P) sensor configured to attach to respiration, vascular pressure and audio points of the mammal in a manner suitable for obtaining the acquired individual sensor electrical signal. The sensor system is configured to attach to alternative locations of the specimen in a manner suitable for obtaining electrical signals in communication with a signal receiver and transmitter. Physiological parameters, such as those associated with vital signs (temperature, pulse, respiration, etc.), can be obtained using the monitoring device and associated sensors.

19 Claims, 9 Drawing Sheets

Related U.S. Application Data

(60) Provisional application No. 60/822,379, filed on Aug. 14, 2006.

(51) Int. Cl.
    *G01K 13/00*     (2006.01)
    *A61B 5/021*     (2006.01)
    *G01K 1/02*     (2006.01)
    *G01K 7/02*     (2006.01)
    *G01K 13/02*     (2006.01)
    *A61B 5/026*     (2006.01)
    *A61B 5/03*     (2006.01)
    *A61B 5/00*     (2006.01)
    *A61B 5/08*     (2006.01)

(52) U.S. Cl.
    CPC ...... *A61B 5/02108* (2013.01); *A61B 5/02141* (2013.01); *A61B 5/03* (2013.01); *A61B 5/0816* (2013.01); *A61B 5/0878* (2013.01); *A61B 5/742* (2013.01); *G01K 1/024* (2013.01); *G01K 7/02* (2013.01); *G01K 13/002* (2013.01); *G01K 13/02* (2013.01); *A61B 5/08* (2013.01); *A61B 5/082* (2013.01)

(58) Field of Classification Search
    USPC .......................................................... 600/549
    See application file for complete search history.

(56) References Cited

U.S. PATENT DOCUMENTS

| | | | |
|---|---|---|---|
| 3,332,286 A | 7/1967 | Strong | |
| 3,336,804 A * | 8/1967 | Poppendiek | A61B 5/028 374/E1.018 |
| 3,626,757 A * | 12/1971 | Benzinger | G01J 5/041 374/130 |
| 3,802,264 A * | 4/1974 | Poppendiek | G01F 1/002 73/204.24 |
| 3,867,205 A | 2/1975 | Schley | |
| 3,942,242 A | 3/1976 | Rizzolo | |
| 3,999,537 A * | 12/1976 | Noiles | A61B 5/02055 374/142 |
| 4,018,624 A | 4/1977 | Rizzolo | |
| 4,191,194 A * | 3/1980 | Watanabe | A61B 5/028 600/505 |
| 4,493,564 A * | 1/1985 | Epstein | A61B 5/024 374/179 |
| 4,527,005 A * | 7/1985 | McKelvey | G01K 7/04 136/221 |
| 4,548,516 A * | 10/1985 | Helenowski | A61B 5/028 374/135 |
| 4,579,002 A | 4/1986 | Zettler | |
| 4,681,099 A | 7/1987 | Sato et al. | |
| 4,705,498 A | 11/1987 | Goss | |
| 4,715,221 A | 12/1987 | Grims et al. | |
| 4,721,589 A | 1/1988 | Harris | |
| 4,757,825 A * | 7/1988 | Diamond | A61B 5/11 340/575 |
| 4,816,197 A | 3/1989 | Nunn | |
| 4,848,147 A | 7/1989 | Bailey et al. | |
| 4,850,217 A | 7/1989 | Nunn | |
| 4,932,250 A | 6/1990 | Assaf et al. | |
| 4,983,336 A | 1/1991 | Langlois | |
| 4,990,193 A | 2/1991 | Kimura | |
| 5,043,023 A | 8/1991 | Bentley | |
| 5,069,222 A * | 12/1991 | McDonald, Jr. | A61B 5/0816 600/537 |
| 5,158,366 A * | 10/1992 | Nagai | F27D 21/0014 338/28 |
| 5,190,048 A * | 3/1993 | Wilkinson | A61B 5/0878 600/537 |
| 5,205,293 A * | 4/1993 | Ito | A61B 5/0265 600/504 |
| 5,320,513 A | 6/1994 | Schmidt | |
| 5,419,858 A | 5/1995 | Hata et al. | |
| 5,427,452 A * | 6/1995 | Stuart | G01K 7/04 136/230 |
| 5,502,292 A * | 3/1996 | Pernicka | B23K 26/24 219/121.63 |
| 5,520,461 A * | 5/1996 | Curry | G01K 7/04 136/232 |
| 5,665,283 A | 9/1997 | Bader et al. | |
| 5,707,659 A | 1/1998 | Erikson | |
| 5,735,280 A * | 4/1998 | Sherman | A61B 17/2202 600/1 |
| 5,772,933 A | 6/1998 | Kotzab | |
| 5,832,592 A | 11/1998 | Bowman et al. | |
| 5,902,252 A | 5/1999 | Hohlfeld et al. | |
| 5,909,004 A * | 6/1999 | Hedengren | G01K 3/14 136/201 |
| 5,937,853 A * | 8/1999 | Strom | A61M 16/00 128/204.18 |
| 5,945,046 A | 8/1999 | Hehl et al. | |
| 5,954,659 A * | 9/1999 | Curley | A61B 5/028 600/504 |
| 5,959,195 A | 9/1999 | Gottfert | |
| 5,967,986 A * | 10/1999 | Cimochowski | A61B 5/0031 600/454 |
| 5,980,237 A | 11/1999 | Swenson et al. | |
| 5,989,192 A * | 11/1999 | Weijand | A61B 5/028 600/504 |
| 5,993,704 A | 11/1999 | Bader et al. | |
| 6,006,601 A | 12/1999 | Osborne | |
| 6,077,228 A * | 6/2000 | Schonberger | A61B 5/411 374/100 |
| 6,077,470 A | 6/2000 | Beaumont | |
| 6,084,174 A | 7/2000 | Hedengren et al. | |
| 6,090,318 A | 7/2000 | Bader et al. | |
| 6,293,700 B1 | 9/2001 | Lund et al. | |
| 6,312,628 B1 | 11/2001 | Wieder et al. | |
| 6,375,621 B1 * | 4/2002 | Sullivan | A61B 5/113 600/484 |
| 6,393,919 B1 | 5/2002 | Ohji | |
| 6,427,690 B1 * | 8/2002 | McCombs | A61M 16/00 128/204.23 |
| 6,464,909 B1 | 10/2002 | Kazmer et al. | |
| 6,487,904 B1 * | 12/2002 | Myhre | G01F 1/684 73/204.12 |
| 6,503,438 B2 | 1/2003 | Beaumont et al. | |
| 6,579,242 B2 | 6/2003 | Bui et al. | |
| 6,629,776 B2 * | 10/2003 | Bell | G01K 7/245 340/539.1 |
| 6,649,095 B2 | 11/2003 | Buja | |
| 6,659,963 B2 * | 12/2003 | Kaufman | A61B 5/01 600/537 |
| 6,854,883 B2 | 2/2005 | Rund et al. | |
| 6,862,932 B2 | 3/2005 | Zimmermann et al. | |
| 7,020,508 B2 * | 3/2006 | Stivoric | A61B 5/0205 600/390 |
| 7,029,173 B2 | 4/2006 | Engel et al. | |
| 7,050,846 B2 | 5/2006 | Sweeney et al. | |
| 7,051,120 B2 | 5/2006 | Greene et al. | |
| 7,052,456 B2 | 5/2006 | Simon | |
| 7,052,465 B1 | 5/2006 | Lunak et al. | |
| 7,055,520 B2 | 6/2006 | Swisa | |
| 7,060,030 B2 | 6/2006 | Von Arx et al. | |
| 7,062,327 B2 | 6/2006 | Bradley et al. | |
| 7,063,669 B2 | 6/2006 | Brawner et al. | |
| 7,064,270 B2 | 6/2006 | Marshall et al. | |
| 7,065,396 B2 | 6/2006 | Hampton | |
| 7,065,409 B2 | 6/2006 | Mazar | |
| 7,128,714 B1 | 10/2006 | Antonelli et al. | |
| 7,181,264 B2 | 2/2007 | Wiesmann et al. | |
| 7,278,937 B2 | 10/2007 | Laliberty et al. | |
| 7,361,830 B2 | 4/2008 | Richetto et al. | |
| 7,585,166 B2 | 9/2009 | Buja | |
| 7,985,185 B2 | 7/2011 | De Voir et al. | |
| 2002/0097155 A1 * | 7/2002 | Cassel | A61B 5/6831 340/573.1 |
| 2002/0123745 A1 * | 9/2002 | Svaasand | A61B 18/203 606/9 |

(56) References Cited

U.S. PATENT DOCUMENTS

| | | | |
|---|---|---|---|
| 2003/0091092 A1* | 5/2003 | Engel | H01L 35/22 374/179 |
| 2003/0209264 A1* | 11/2003 | Richetto | G01K 7/02 136/224 |
| 2004/0170213 A1* | 9/2004 | Rund | G01K 15/00 374/170 |
| 2004/0185142 A1 | 9/2004 | Olaru | |
| 2004/0215098 A1* | 10/2004 | Barton | A61B 5/0008 600/549 |
| 2004/0238023 A1 | 12/2004 | Richetto et al. | |
| 2004/0249296 A1* | 12/2004 | Ellscheid | A61B 5/02455 600/514 |
| 2005/0277872 A1* | 12/2005 | Colby | A61B 5/0022 604/67 |
| 2006/0206029 A1 | 9/2006 | Yair | |
| 2006/0246167 A1* | 11/2006 | Buja | B29C 45/77 425/144 |
| 2006/0253300 A1 | 11/2006 | Somberg et al. | |
| 2007/0028625 A1* | 2/2007 | Joshi | F23C 13/04 60/777 |
| 2007/0106172 A1* | 5/2007 | Abreu | A61B 5/0002 600/549 |
| 2007/0118045 A1* | 5/2007 | Naghavi | A61B 5/01 600/549 |
| 2008/0081963 A1 | 4/2008 | Naghavi et al. | |
| 2008/0214951 A1* | 9/2008 | Fritz | A61B 5/01 600/549 |

FOREIGN PATENT DOCUMENTS

| | | |
|---|---|---|
| WO | WO 0236326 | 5/2002 |
| WO | WO 2008022122 | 2/2008 |

OTHER PUBLICATIONS

Prosecution History for U.S. Pat. No. 6,649,095.
Prosecution History of Related U.S. Appl. No. 11/838,491, filed Aug. 14, 2007 (US Publication 20080039739).
PCTUS2001046619_WO2002036326 An Unofficial International Preliminary Report on Patentability Dated Feb. 7, 2003 for PCT/US2001/046619 Filed Nov. 5, 2001, Published May 10, 2002, As WO/2002/036326; Inventor: Frederick J. Buja; Corresponding to U.S. Pat. No. 6,649,095.
PCTUS20070775894_WO2008022122 An Unofficial The International Preliminary Report on Patent Ability Date Feb. 17, 2009 for PCT/US2007/075894, Published Feb. 21, 2008 as WO 2008/022122; Corresponding to U.S. Appl. No. 11/838,491; Inventor Frederick J. Buja.
Morgan, E. S. "The Effect of Stress on the Thermal E.M.F. of Platinum-Platinum/13% Rhodium Thermocouples", 1968, J. Phys. D: Appl. Phys. 1, 1421-1429.
Baldes, E.J. "Micromethod for Measuring Osmotic Pressure"; J. Sci. Instrum. 11, 223-225.
Birch, F. "Thermoelectric Measurement of High Temperatures in Pressure Apparatus", Rev. Sci. Instrum. 10, 137-140, (1939).
Bloch, F. et al. "Effect of Pressure on EMF of Thermocouples", J. Appl. Phys. 38, 409-412 (1967).
Waxman, M and Hastings, R. J.; "Proposed Experiment to Determine the Effect of Pressure on the EMF of Thermocouples"; J. Appl. Phys. 43, 2629-2632 (1972.
Hanneman, R. E. and Strong, H. M. "Pressure Dependence of the EMF of Thermocouples to 1300° C. and 50 Kbar"; J. Appl. Phys. 36, 523-528 (1965).
Zanstra, P. E. "Welding Uniform Sized Thermocouple Junctions From Thin Wires"; 1976 J. Phys. E: Sci. Instrum. 9, 526-528.
Eisner, A. D. "Design and Development of a Micro-Thermocouple Sensor for Determining Temperature and Relative Humidity Patterns Within an Airstream": Journal of Biomechanical Engineering; Nov. 1989, vol. 11; 283-287.
Bundy, F. P., "Effect of Pressure on EMF of Thermocouples", J. Applied Phys. 32, 483-488 (1961).
U.S. Appl. No. 13/108,906—An Unofficial Prosecution History as of Sep. 9, 2014 for U.S. Appl. No. 13/108,906, filed May 16, 2011, Published Nov. 17, 2011, as US-2011-0282163-A1; Inventor: Frederick J. Buja.
Bader, C.; Burkhart, C.; König, E.; "Controlled Conditions"; Kunstoffe Plast Europe Jul. 2007; c. Carl Hanser Verlag, Münich.
Buja, F.J.; Establishing the molding Process and Molded Product "Consistency"; Revised Jun. 1990; Presented last by F.J. Buja in Chicago at National Plastics Expo, Jun. 1994 p. 1-43.
Buja, F.J.; Establishing the molding Process and Molded Product "Consistency"; Revised Jun. 1990; Presented last by F.J. Buja in Chicago at National Plastics Expo, Jun. 1994 p. 44-101.
Digital Optics Corporation; Standard Processes Oct. 19, 2004; Process Specification Sheet; 1 page; Digital Optics Corporation, 8701 Mallard Creek Road, Charlotte, NC 28262, USA; 704-549-5556.
Dynisco; Heaterless Injection machine Nozzles; Dynisco Instruments; www.dynisco.com.
Dynisco; Technical Reference; "Using Pressure Transducers to Improve Control of the Extrusion Process"; pp. 170-174.
Kistler; Nozzle Pressure Measuring Chain for Injection Molding Machines;.
Kistler; P-T Sensor for Molding Cavity Pressure and Temperature.
Koelsch, J.R., Contributing Editor; "Temperature control Builds Better Injection Molding"; Quality Magazine; May 2000; www.qualitymag.com/articles/2000/may00/0500f3.asp.
Love, A.; A Treatise on the Mathematical Theory of Elasticity; 4$^{th}$ Edition Revised; c. 1927; ISBN 0-486-60174-9; Dover Publications, Inc. Mineola, NY 11501; pp. 6-13; 92-94; 117; 140-141;146-151.
Nanmac; "Selecting the Right Thermocouple: There are more choices today"; Reprinted from Plastics Technology; NANMAC Corporation; www.nanmac.com ; c. 1998.
Noral; Temperature Sensors for Industry; www.noraltemperaturesensor.com ; Noral, Inc.
Rosato, D.V. and Rosato, D.V.; Injection Molding Handbook; 2 nd Edition; ISBN 0-412-99381-3; pp. 512-547 ; c. 1995 Chapman & Hall, New York, NY.
Rosato, D.V. and Rosato, D.V.; Injection Molding Handbook; 2 nd Edition; ISBN 0-412-99381-3; pp. 548-580 ; c. 1995 Chapman & Hall, New York, NY.
Sheth, H.R.; Nunn, R.E.; An Adaptive Control Methodology for the Injection Molding Process, Part 2: Experimental Application; University of Massachusetts Lowell, Department of Plastics Engineering, Lowell MA.
The Merck Manual of Diagnosis and Therapy; 18$^{th}$ Edition; C. 2006 Merck & Co., Inc.; pp. 589-596; pp. 2549-2550.
"Correlation of Blood Temperature Fluctuations with Blood Pressure Waves," Appelbaum A. et al. Basic Research in Cardiology, 77 93-99 (1982).
Webster's II New Riverside University Dictionary, 1994 p. 159 and 749.
Webster's II New Riverside University Dictionary, 1994 p. 1190.
Buja, F. J.; Using Mold Opening to Relate the Molding Process to Molded Product; KTechnologies c. 1986.
The Merck Manual of Diagnosis and Therapy; 18$^{th}$ Edition; C. 2006 Merck & Co., Inc.; pp. 589-596; pp. 2549-2550.

* cited by examiner

SYSTEM AND METHOD EMPLOYING A THERMOCOUPLE JUNCTION FOR MONITORING OF PHYSIOLOGICAL PARAMETERS

This application is a continuation of and claims priority from co-pending U.S. application Ser. No. 11/838,491 for a "SYSTEM AND METHOD EMPLOYING A THERMOCOUPLE JUNCTION FOR MONITORING OF PHYSIOLOGICAL PARAMETERS," filed Aug. 14, 2007 by Frederick J. Buja, and also claims priority from U.S. Provisional Application 60/822,379 for a "SYSTEM AND METHOD FOR MONITORING OF PHYSIOLOGICAL PARAMETERS," filed Aug. 14, 2006 by Frederick J. Buja, both of which are hereby incorporated by reference in their entirety.

Cross-reference is made to U.S. application Ser. No. 13/108,906 for a "SENSOR," filed May 16, 2011 by Frederick J. Buja, which further claims priority from U.S. Provisional Application 61/334,828 for a "SENSOR," filed May 14, 2010 by Frederick J. Buja, and to U.S. patent application Ser. No. 11/381,246 for a "SYSTEM AND METHOD FOR MONITORING TEMPERATURE AND PRESSURE DURING A MOLDING PROCESS," by Frederick J. Buja, filed May 2, 2006, which claims priority from U.S. Provisional Application 60/676,761 for a "MELT DENSITY SENSING SYSTEM AND METHOD," by Frederick J. Buja, filed May 2, 2005, and from U.S. Provisional Application 60/745,871 for a "MEANS TO SENSE AN INJECTED MELT FLOW FRONT CAVITY GAS VENTING AND PEAK MELT DENSITY POINT AND TIME TO FORM A MOLDED PART," by Frederick J. Buja, filed Apr. 28, 2006, and all the listed applications are hereby incorporated by reference in their entirety.

The embodiments disclosed herein are directed to a system and method for monitoring of physiological parameters, and more particularly to a system employing an improved, low-cost thermocouple sensor bead to accomplish sensing of temperature and/or pressure variations, using invasive or non-invasive means.

COPYRIGHT NOTICE

A portion of the disclosure of this application document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND AND SUMMARY

Based upon improved thermocouple sensing technology, as described for example in co-pending U.S. application Ser. No. 11/381,246, various alternative uses and embodiments have been contemplated. The embodiments include, among others, the application of improved thermocouple technology to uses in medical or physiological sensing devices. Moreover, alternative or additional sensing devices (e.g., piezoelectric accelerometer) for sensing falls or sudden changes to the wearer may also be included in the series of sensors that are contemplated for sensing physiological parameters. The following patents are also hereby incorporated by reference in their entirety: U.S. Pat. Nos. 6,649,095, 7,050,846, 7,051,120, 7,055,520, 7,060,030, 7,062,327, 7,063,669, 7,064,270, 7,065,396, and 7,065,409.

In one embodiment, the disclosed system and method may be used to sense temperature and pressure of a specimen (e.g., a mammal) in a physiological setting. As disclosed herein, such sensing may be accomplished through non-invasive or invasive techniques. In those situations where direct exposure of the thermocouple junction is not possible, the junction may be encapsulated in a flexible, thermally-conductive covering so as not to impede the sensing of pressure and temperature variations. It should be appreciated that a thermocouple formed with a generally-spherical, micro-bead type junction may be employed to sense not only changes in temperature, but also localized changes in pressure. In such embodiments, the reduced-size thermocouple junction is preferably exposed to the physiological environment it is designed to sense in order to reliably provide a signal response to changes in temperature and/or pressure. As discussed below, the response of the micro-bead thermocouple (e.g., a bead formed by laser welding of 0.010 inch thermocouple wires made from iron, and constant an or other known thermocouple combinations) is capable of sensing both temperature and pressure components.

Disclosed in embodiments herein is a physiological sensor, comprising: a thermocouple having a bead-shaped junction suitable for exposure to a physiological processes, whereby the junction can sense a physiological parameter, said thermocouple producing a signal in response to the physiological parameter; and circuitry connected to the thermocouple for receiving the signal, converting the signal to data representing the physiological parameter, and at least temporarily storing data representing the physiological parameter.

Further disclosed in embodiments herein is a method for sensing a physiological parameter, comprising: providing a thermocouple including a bead-shaped junction suitable for exposure to a physiological processes; exposing the bead-shaped junction to the physiological process, whereby the junction produces a signal in response to the physiological parameter; receiving the signal; converting the signal to data representing the physiological parameter; and at least temporarily, storing data representing the physiological parameter.

The various embodiments described herein are not intended to limit the invention to those embodiments described. On the contrary, the intent is to cover all alternatives, modifications, and equivalents as may be included within the spirit and scope of the invention as defined by the appended claims.

DETAILED DESCRIPTION

As more particularly set forth below, the disclosed system and methods are directed to physiological sensors for use on humans and similar mammalian specimens. Although described with respect to non-invasive embodiments, the disclosed systems and methods may be employed with more invasive techniques in a similar manner.

Figure 1:
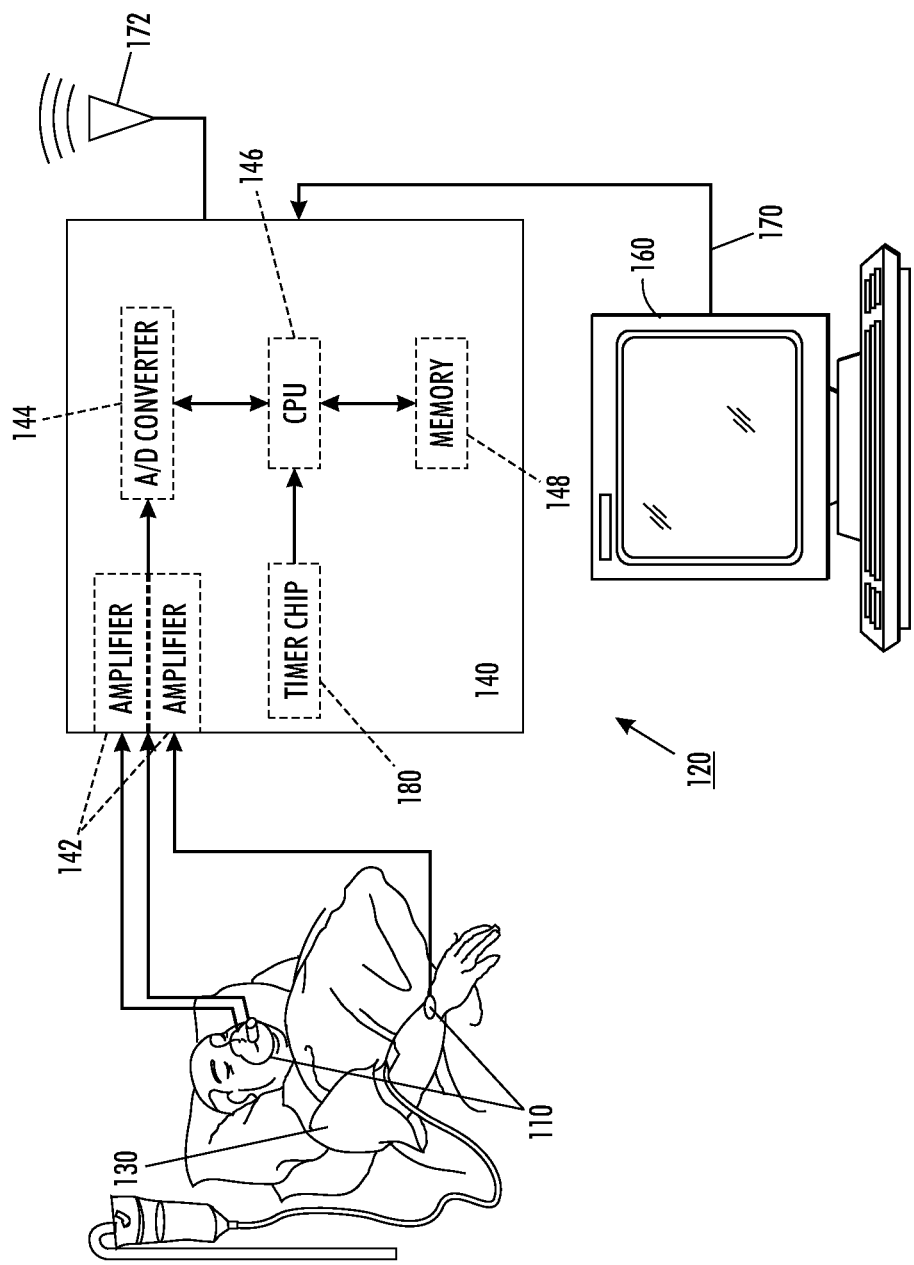
FIG. 1 is a block diagram illustrating various components in a system for sensing physiological parameters.

Referring to FIG. 1, there is depicted a block diagram of a physiological sensor 110 in a monitoring system 120 for a human 130. The sensor includes at least one thermocouple having a bead-shaped junction suitable for exposure to a physiological process(es), whereby the junction can sense a physiological parameter, the thermocouple producing a thermal energy work signal in response to the physiological parameter such as the specimen's temperature, pulse rate, etc. The sensor provides an output signal from the thermocouple junction in the form of a voltage ($V_{emf}$), that is passed to circuitry 140 for processing. In one embodiment, the circuitry may include an amplifier(s) 142 for amplifying the EMF voltage ($V_{emf}$), and an analog-to-digital (A/D) converter 144 for converting the $V_{emf}$ to a digital value or representation. Under the control of a processor or CPU 146, the data is collected from the A/D converter and at least temporarily stored in memory 148, and may be subsequently processed and transmitted, etc. As will be discussed relative to the processes described below, the processor 146 may perform various calculations to both adjust the readings as well as to provide desired physiological output. For example, in addition to converting the voltage to a temperature, the system also corrects the temperature to a standard ambient condition (e.g. 14.7 psi pressure).

As also depicted in FIG. 1, the system 120 may include one or more workstations, or similar handheld computing devices (e.g., Blackberry™, Palm Pilot™, iPOD™) that interface or at least receive the data from circuitry 140. In one embodiment, the workstation 160 may also provide programmatic control software to the processor 146 through wired 170 (direct serial, parallel, USB, network) or wireless 172 (infrared, radio frequency, Bluetooth™, etc.) communications means or links. Similarly, the workstation or handheld device may permit a user to control operation of the system, including the frequency of monitoring (continuous, periodic, based upon a trigger point, etc.), the amount of data to store (e.g., all, last five readings, etc.), the method for transmission of data, as well as specimen data (name, patient identification code, etc.). Although not depicted it will be appreciated that conventional interface components and circuitry may be employed to accomplish one or more alternative communications links within the system of with external devices to which the system may send physiological parameter data.

Relative to the workstations or handheld devices, it should be appreciated various instruments are suitable for receiving signals produced by one or more of the sensors described herein and logging or otherwise recording the signals. The instruments may further include the ability to display data that is representative of the signals (processed and unprocessed), e.g., over time. As will be appreciated, it may be necessary to precondition or otherwise process the signals from the various sensing devices. For example, it may be necessary to provide amplification or similar processing in relation to the thermocouple signals generated.

Returning to the example above, the sensor may provide, via a thermocouple bead sensor 110 placed in or near the patient's mouth, the physiological parameter of body temperature. Here again, the circuitry stores data over a period of time to sense changes in temperature and to thereby represent a physiological process. In a further contemplated embodiment, the sensors 110 may be employed to sense temperature at a plurality of sites or locations in or on a specimen.

Figure 2:
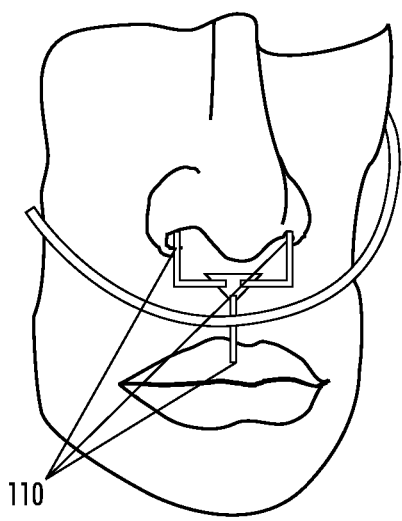
FIGS. 2 and 3 are exemplary illustrations of several embodiments for the placement of sensors.
Figure 3:
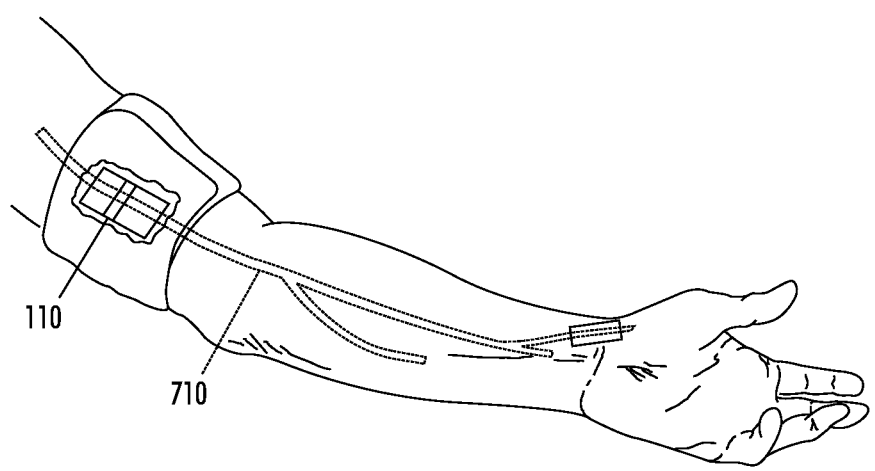

In the examples set forth in FIGS. 2 and 3, alternative sensor placement and types are illustrated. FIG. 2, for example, depicts the placement of an array of three thermocouple bead sensors 110 in the respective nasal and mouth area in order to sense the respiration of a specimen. Such an array of thermocouple bead sensors may be employed to sense respiration from multiple orifices (e.g., nose, mouth) similar to the respiration sensing suggested in U.S. Pat. No. 5,832,592, issued Nov. 10, 1998. FIG. 3 is one example of a sensor that may be placed next to an artery of a specimen in order to sense pulse or blood pressure and the like.

Figure 4A:
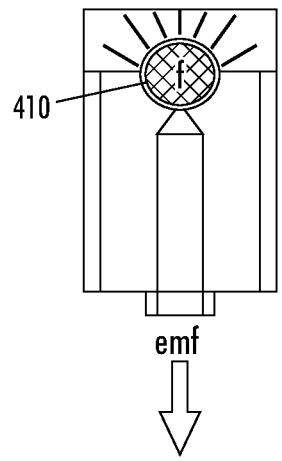
FIGS. 4A and 4B are illustrations of the thermocouple micro-bead in accordance with the disclosed embodiments.
Figure 4B:
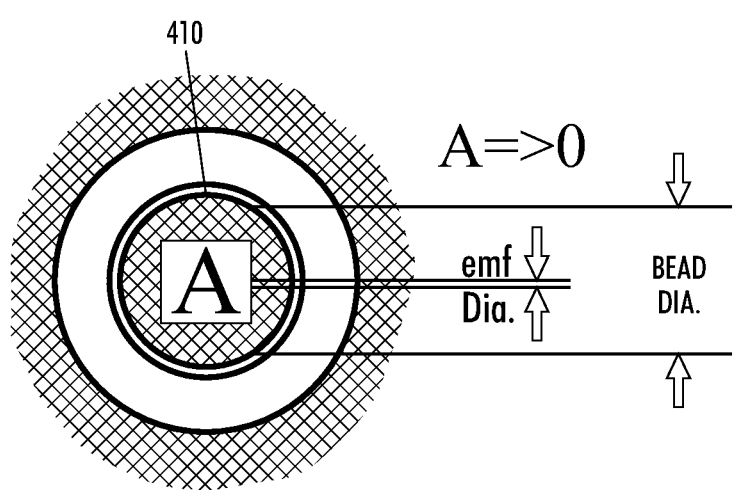

As depicted for example in FIGS. 4A and 4B, the bead-shaped junction 410 is a micro-bead where the thermocouple senses changes in a thermo-mechanical response as an expansion/contraction from heat and compression decompression of pressure exerted on the bead-shaped junction, thereby producing a signal including a pressure component. In other words, the response of the micro-bead junction includes an enhanced or amplified pressure response, from the response of the bead surface area, so that the pressure and temperature may be both be sensed simultaneously. Thus, the sensor generates, through the micro-bead junction, a thermo-mechanical response that includes a response to an encompassing gas, liquid, or solid pressure fluctuation. It will be recognized that the micro-bead may be formed as a contact region between two dissimilar metal wires (e.g., iron and constant an) that produce a varying voltage in response to changes in temperature and pressure. Moreover, at least one of the dissimilar metal wires has a generally round cross-section. As illustrated in FIG. 4B, the contact is a welded contact, preferably welded using a low-power laser so as to minimize the size and inner core density (K) change of the thermocouple junction and the associated or surrounding bead. The response of the sensor bead to pressure (mechanical) variability is believed to be significantly enhanced by reducing the size of the bead. Thus, micro-beads having small diameters are believed preferable. Ranges of micro-bead diameters on the order of 0.10 inches and smaller are believed to be preferable, and micro-beads having sizes of about 0.001-0.010 may prove to provide suitable responses.

In one embodiment, the sensor employed for sensing pressure, temperature, etc. may be a sheathed sensor with a 0.060" diameter, which can be purchased from Omega with stripped wire ends suitable for welding. In accordance with U.S. application Ser. No. 11/381,246 (Publication 2006/0246167 A1), by Frederick Buja, hereby incorporated by reference in its entirety, the thermocouple is preferably formed with a micro-bead junction, wherein the smaller the bead size, the more sensitive the junction is to changes at the bead surface to temperature and pressure, etc. More specifically, the response of the micro-bead junction is a combination of the temperature and pressure fluctuation acting as work energy on the EMF junction. The strain of the spherical bead is directed to the EMF junction. As a further illustrative example, consider a bead surface area change from MEAN Diameter=Pi·D²±ΔD. The area Increase is not equal to the change from nominal by the factor +2ΔD² or (D±ΔD)², where (D+ΔD)²=2D²+2ΔD+ΔD² and (D−ΔD)²=2D²−2ΔD+ΔD². Rather the area is smaller by the same that the ±2ΔD factor, but the smaller area is less by a +ΔD² exponential ratio, thereby leading to force concentration and responsiveness to pressure variations. Where the junction size decreases from compression of the bead, the pressure sensed on the junction of the thermocouple is effectively increased, wherein the traditional thermocouple junction further becomes sensitive to pressure changes as well as temperature changes, and can produce signals indicative thereof. In other words, the micro-bead junction is believed to produce a significant EMF response to both changes to temperature as well as pressure.

Figure 5A:
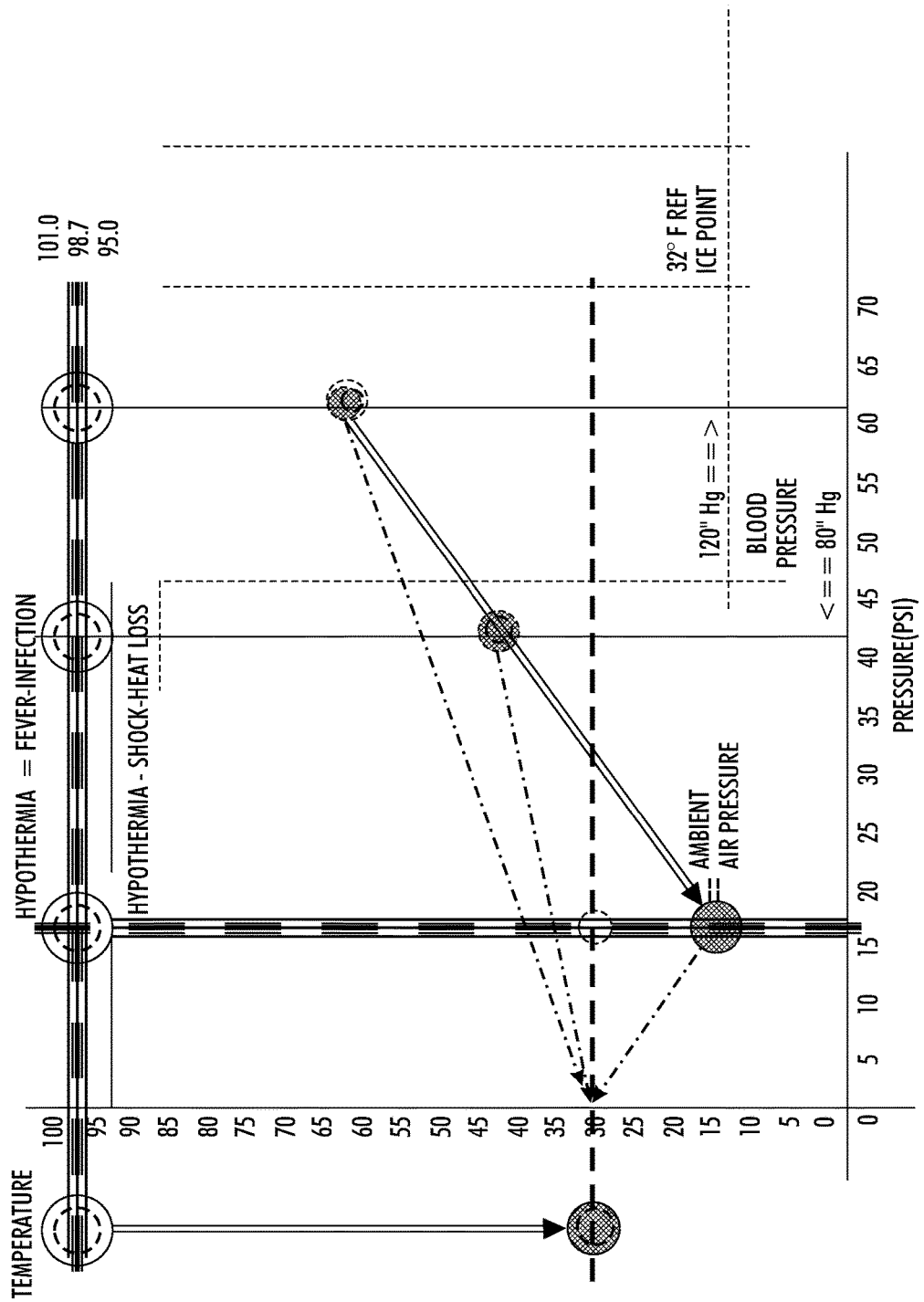
FIG. 5A is a graphical illustration of the relationship between temperature and pressure on the micro-bead junction.
Figure 5B:
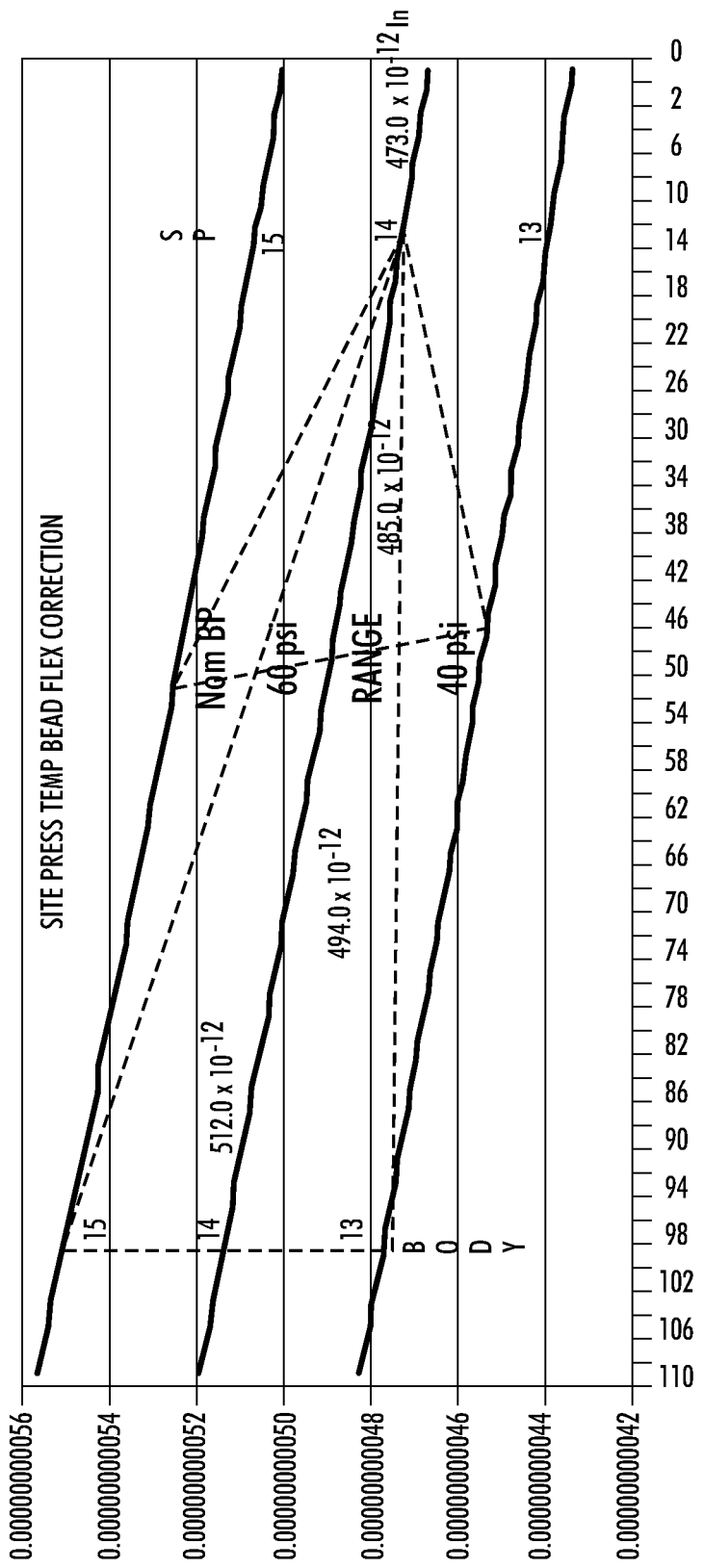
FIG. 5B is a graphical illustration of a manner in which the micro-bead thermocouple may be "calibrated" for a particular ambient environment.

Considering the thermal-mechanical response of the micro-bead thermocouple, the response may be predicted in terms of thermal-mechanical flex ($_BZ$) in relation to the illustrations found in FIGS. 5A-B.

$$_BZ_{eE} = \text{Thermal-Mechanical Flex} = {_BT_e \cdot _BM_E};$$

$$\Delta_B L_E/\pi(\text{Spherical Bead}) = \Delta_B D_E;$$

$$_AF_{G,L,S} = {_AP_{G,L}} \cdot {_{SB}A_{E0}}, \text{ representing applied bead surface force}$$

$$_BZ = [_BCD_{eE}@_{T=0} + (_BmD_{eE} \cdot _BT_{eactual})] \cdot [(_BD_{E0} \cdot _AF_{G,L,S})/(_BA_{E0} \cdot _BD_E)];$$

$$_BZ = [_BC_{eE}@_{T=0} + (_Bm_{eE} \cdot _BT_{eactual})] \cdot [(_AP_{G,L,S} \cdot _BD_{E0})/(_BD_E)];$$

$$_AF_{G,L,S} = {_AP_{G,L,S}} \cdot {_BA_{E0}}$$

$$_BK_{eE} = \text{Bulk Modulus\#/ln}^3 \text{ Volume} = \text{FORCE on Bead};$$

where matter D is bead diameter, state $(_A) = _AG = $ Gas, $_AL = $ Liquid, $_AS = $ Solid. For Thermal $_B(e)$ Linear Flex and Mechanical $_B(E)$ Linear Flex, the relationships may respectively be stated as:

$$_BL_e = \text{Circumference} = \pi \cdot _BD_e \text{ and}$$

$$_BL_E = \text{Circumference} = \pi \cdot _BD_E.$$

Therefore, in a spherical bead the

Thermal Diameter $= {_BD_e} = {_BL_e}/\pi;$ and the

Mechanical Diameter $= {_BD_E} = {_BL_E}/\pi$

More specifically, the Spherical Bead ($_B$) Thermal Flex is characterized as:

Diameter $\Delta_B D_T \approx _BD_{0T} \cdot [1 + (_BDe \cdot \Delta_B T)]$

Area $\Delta_B A_T \approx _BA_{0T} \cdot [1 + (2 \cdot _BDe \cdot \Delta_A T)]$ Volume $\Delta_B V_T \approx _BV_{0T} \cdot [1 + (3 \cdot _BDe \cdot \Delta_A T)]$ where $_BT_{Afinal} - {_BT_{Aactual}} = \Delta_B T_{Arange}$, and $$_BD_e = {_BC_e}@_{T=0} + (m_BDe \cdot _BT_{actual})$$

where $_BCe@_{T=0} = 0.000006$ ln/in/° F.

$m_Be = 0.000\ 000\ 0023''/°$ F.

therefore at $_BT_{eactual} = 0°$ F., $_BT_e = 0.000006$ in./° F./in.

and $_BT_{actual} = 900°$ F., $Ta = 0.0000087$ in./° F./in.
0.000006''+2.07×10⁻⁶

And, the Spherical Bead ($_B$) Mechanical Flex is characterized as:

$$_B\Delta D_E = (_BD_0 \cdot _AF_{G,L,S})/(_BA_{E0} \cdot _BD_E) \text{ With } _AF_{G,L,S} = {_AP_{G,L,S}} \times {_BA_{E0}}$$

$$_B\Delta D_B = (_BD_0 \cdot _AP_{G,L,S})/(_BD_E)$$

therefore strain of enclosing substance $_AP_{G,L,S} = {_BD_E} \cdot (_B\Delta D_B/_BD_0)$ where $_B\Delta D_E = {_BC}@_{T=0} + (_BE \cdot _BT_{Eactual})$ $_AF_G, _AF_L, _AF_S$, <==enclosing matter on sensor bead where $_BD_E@_{T=0} = 30,000,000\#/\text{ln}^2$ and $m_BDe = (25,000,000 - 30,000,000\#/\text{ln}^2) = -(5,000,000/900° F.) \cdot _BT_{actual}$ where $_BD_E@_{T=900} = 30,000,000\#/\text{ln}^2 - 5,000,000\#/\text{ln}^2 = 25,000,000\#/\text{ln}^2$ Referring to FIG. 5B, as a result of calibrating the bead to known temperature reference ice point (32° F.) and boiling point (212° F.) at an atmospheric pressure of about 1 Bar (14.7 psi) the thermal-mechanical (thermal flex) verification and certification can be accomplished, The response of the micro-bead thermocouple may be "corrected" to adjust for changes in atmospheric site pressure. FIG. 5 is a chart illustrating an exemplary correction for variations in pressure and temperature.

In one embodiment, the dissimilar metal wires have a diameter of less than about 0.006 inches. More specifically, the dissimilar metal wires may have a diameter of no larger than about 0.001 inches. In a cross-wire junction, where the contact that forms the EMF junction is not welded but is formed primarily through contact, the contact region may be less than about 0.000001 square inches in size.

Referring again to FIG. 1, the circuitry may also include a timing circuit or chip 180. One use of such a circuit may where the bead-shaped thermocouple junction is placed in proximity to a specimen's respiratory orifice(s) as in FIG. 2, to sense respiration. There the circuitry would output data including a respiration rate based upon timing data from the chip 180. Another alternative use of the timing capability may be to date/time stamp data produced by the circuitry. Yet another use of the timing chip is as a trigger for sensing one or more pf the physiological parameters being monitored (e.g., pulse and blood pressure every 15 minutes) Although separately depicted, the timing chip or circuitry may reside on the processor or in other components of circuitry 140 or system 120. Furthermore, those familiar in the design of such logic and control circuitry will appreciate that circuitry 140 will also include a power source, interconnecting ports (plugs, jacks and the like), and other components to facilitate interchange of signals and data as described herein. The various interconnections between the components are illustrated with single-line arrows, but are not intended to be limited to such construction and indeed the components may be connected in a printed circuit or other circuitry and may include multi-trace connections, a bus structure or other means for interconnecting the components. One embodiment also contemplated is the use of amplifiers and other circuitry components at the sensor location in order to make the sensors self-powered and suitable for remote monitoring by a more centralized system. Moreover, such a system may use telemetry or similar technology to periodically communicate with the sensors, thereby allowing the specimen being monitored to move about.

Figure 6:
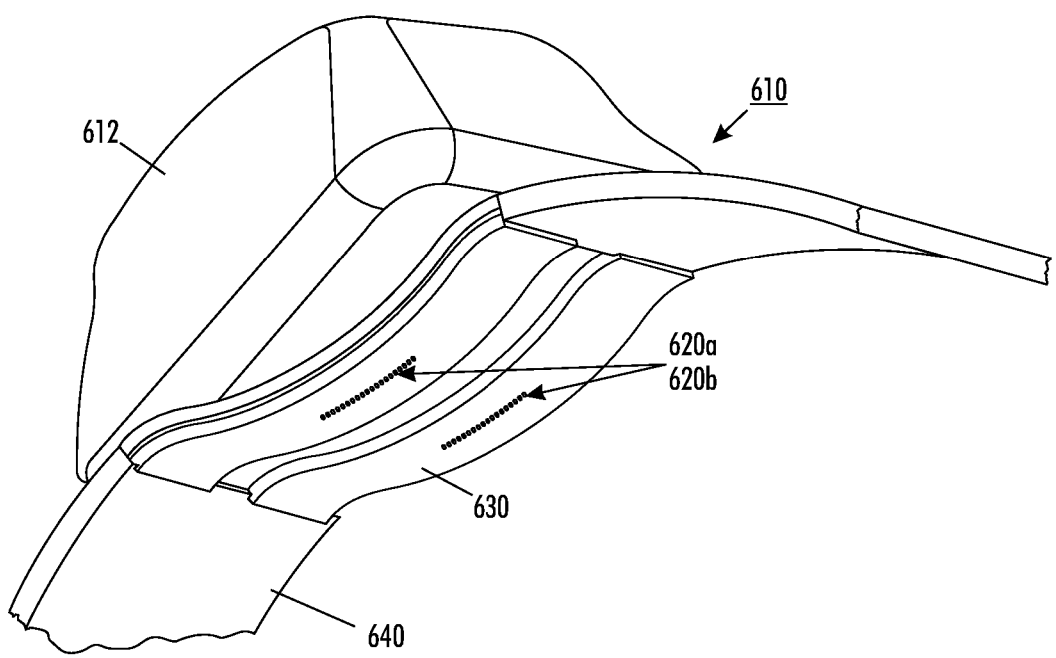
FIG. 6 is an illustrative view of an embodiment of the disclosed system and method for sensing various parameters including blood pressure and fluid flow rate.

As depicted in FIG. 3, for example, another embodiment contemplates the timing device 180, where the bead-shaped junction is placed in proximity to an artery of a specimen to sense changes in the pressure of the artery. Based upon the sensing of pressure change, which indicates pumping of the heart muscle, the circuitry processes and outputs data including and indicating the specimen's heart rate. In yet a similar embodiment, a plurality of sensors may be used to provide data on blood pressure and the flow of blood in an artery. For example, referring to FIG. 6, there is depicted a remote, self-contained blood-pressure sensor 610 that may be applied to a specimen's forearm (wrist) or similar location. The sensor includes a housing 612 that encompasses components of the circuitry described above, but in this embodiment is capable of regularly receiving signals from a plurality or array of micro-bead thermocouples 620a and 620b. The array of sensors detect temperature and pressure changes as described above, and the array would include two "lines" of between about ten and twenty, or more, regularly-spaced thermocouple sensors as described above. In one version of the depicted embodiment, a resilient or spring-like member 630 is employed in a slightly convex configuration to assure that when worn by a specimen, the thermocouple junctions remain in proximity to or in contact with the skin and an underlying artery. Lastly, the housing and sensors are attached to the specimen's arm using an arm or wrist band 640, where the ends of the band may be connected when in use via hook and loop type fastener (e.g., Velcro™) snaps or similar disengageable fasteners not shown).

Figure 7:
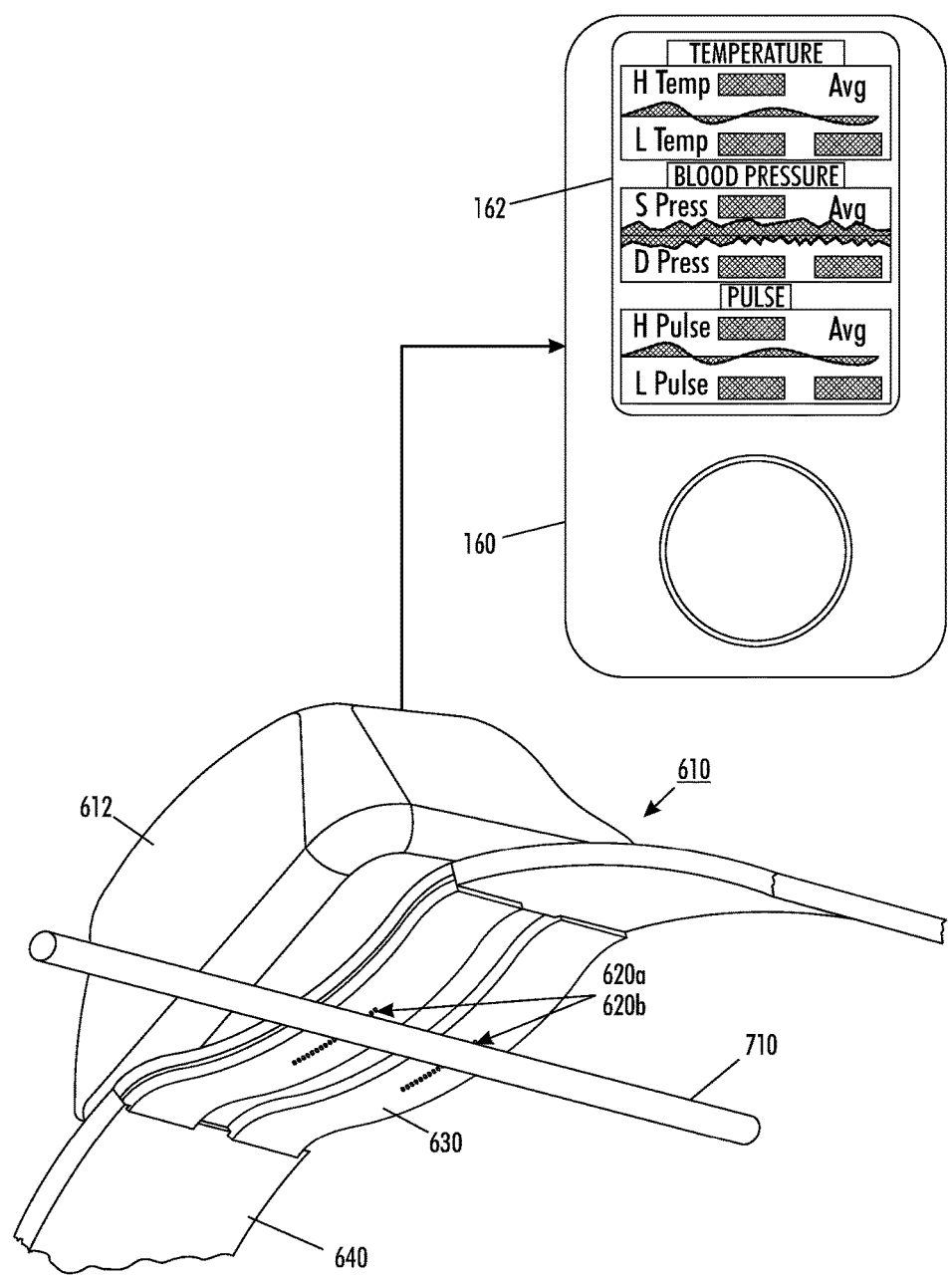
FIG. 7 is a further illustration of the device of FIG. 6 showing additional system features and functionality.

FIG. 7 provides an illustrative example of the relationship of the thermocouple arrays 620a and 620b with an artery 710. It is preferable that the arrays be generally perpendicular to the artery for placement, so that the separation distance between the arrays 620a and 620b may be employed to determine flow rate (e.g., time for a pulse to propagate from sensing by first array (620a) to the second array (620b)). The distance between each of the plurality of sensors in the arrays is either known or can be calculated based upon the spacing within the line of sensors and the separation of the two lines of sensors.

As a self-contained sensor, the device 610 can also exchange data with a workstation or portable computing device 160. And, as illustrated in the display region of the device 160, the user or medical personnel may view the data generated by the sensors in a convenient format. More specifically, display 162 may include one or more charts or graphs depicting processed sensor data over time, thereby showing the changes or trends in the specimen's physiological processes. It will be appreciated that such systems may be contemplated for patient monitoring and the like. Having described one embodiment, the collection and processing of data for illustration in display 162 will now be described in more detail.

Figure 8A:
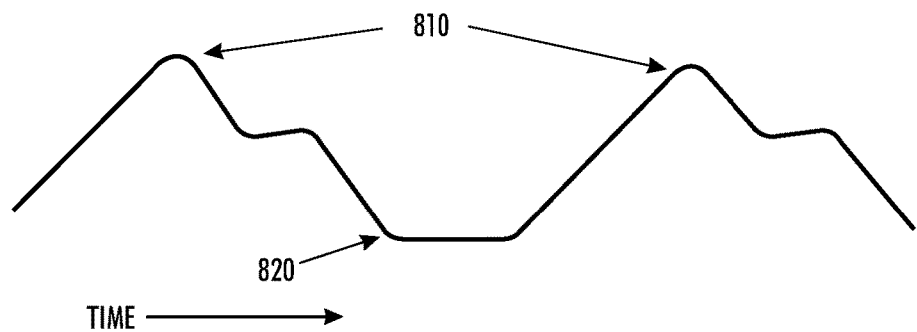
FIGS. 8A and 8B are illustrative examples of a pressure profile that may be generated in accordance with the embodiment depicted in FIG. 6.

Sensing of the temperature from one of more of the micro-bead thermocouple junctions is primarily an operation of collecting data from one of said junctions over time. Sensing the pulse (heart rate) and blood pressure are slightly more involved, and require further processing of the signals and data from the arrays and will now be described. Referring briefly to FIG. 8A, there is depicted a typical sensor profile from a single micro-bead thermocouple. The profile exhibits successive peaks 810 that are indicative of the thermo-mechanical characteristics sensed by the micro-bead junction. The peaks 810 are representative of the maximum pressure exerted on the sensor by the artery, when the artery is likewise expanded in response to pumping or pulsing of the heart. Thus, the peaks are representative of the heart and the associated or relative pressure at which it pumps. Similarly, the base-line 820 is indicative of the artery pressure at rest. It will be appreciated that the sensors may be used to indicate relative changes in pressure or temperature over time, or they may be "calibrated" by taking equivalent pressure readings at the beginning of a sensing session and then the data merely tracks changes in the pressure over time. Alternatively, an additional pressure or thermal sensor may be employed to correct or permit adjustment for changes in ambient pressure or temperature.

Figure 8B:
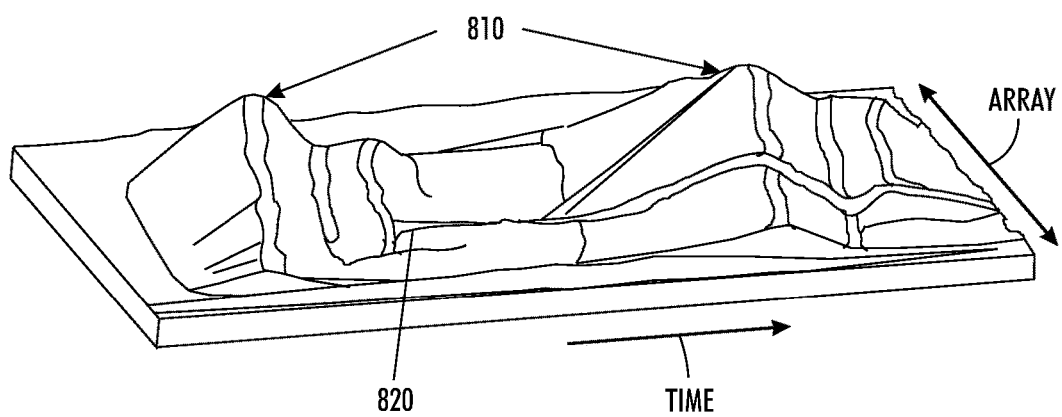
Figure 9:
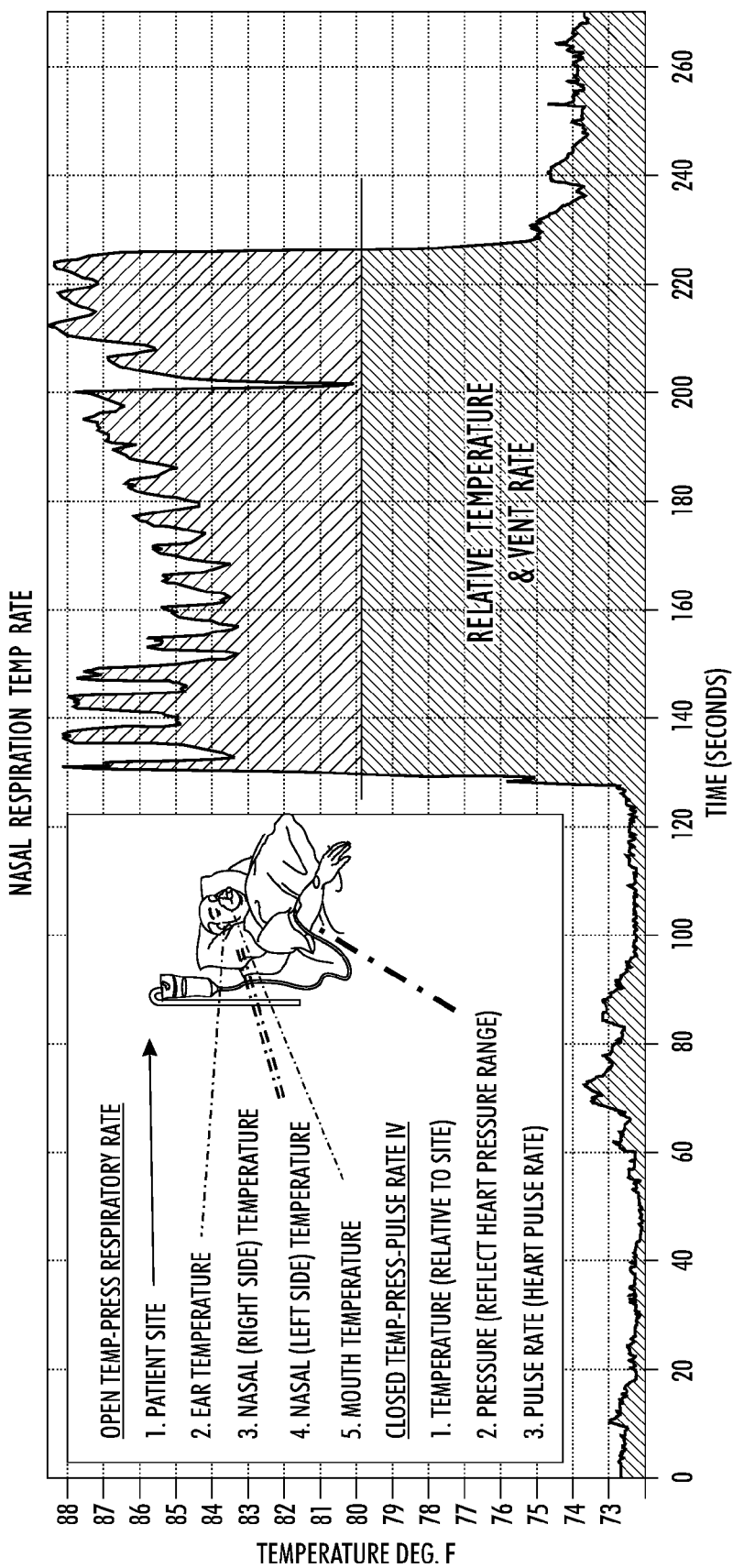
FIG. 9 is an illustrative example of respiration data acquired in accordance with the disclosed system and methods.

A profile such as that depicted in FIG. 8A, when taken across a plurality of sensors in array 620a or 620b, may produce a plot as depicted in the three-dimensional profile of FIG. 8B. In FIG. 8B, it can be seen that there is a central region in which the pressure sensed is greatest, and the pressure tails off to either side (front-back). Such a profile would suggest that the artery is under the approximate middle of the array and that the signals from the arrays sensing the peak data may be employed to calculate and monitor the blood pressure and heart rate. Conversely, the sensors on the extremes of each array have little or no change in signal level due to the heart pumping, and should be used as indicators for the localized temperature readings. To determine the blood pressure then, the system processes the profiles generated by those sensors determined to be located on or closest to the artery (having greatest pressure swings with heart pumping). The signals of such a sensor(s) are then employed to produce resulting pressure data and to produce corresponding systolic (max.) and diastolic (min.) pressure fir each heart pumping cycle. These pressure can be stored and saved in memory so as to permit further processing and display as shown in the middle chart or graph in display 162 (FIG. 7). Similarly, the pulse or heart rate can be calculated based upon the time interval between successive peaks (or a plurality of contiguous peaks), and this information can also be periodically stored and represented in the display 162, where the pulse rate is illustrated in the lower portion of the display. It is further contemplated that rather than a table or chart, various of the physiological parameters discussed herein may be displayed as simple numbers reflecting the current or most recently measured state. In a numeric display it may also be advantageous to show the associated maximum and/or minimum values as well so that a medical practitioner has a better sense for the information being review.

In yet another embodiment of the system, the device may provide a plurality of spaced-apart sensors and a timing device, where bead-shaped junctions for each of said thermocouple sensors are placed in proximity to an artery of a specimen and said circuitry outputs data including a flow rate of blood flowing through the artery. The flow rate would be determined by the delay between sensing say a peak for each heart pulse on the first array and the second array. Knowing the spacing between the arrays (more specifically between the sensors on the arrays via a vectorial distance calculation), the system can determine the time required for the blood pulse (artery pressure surge) to propagate through the artery and thereby estimate the flow rate.

In accordance with the embodiments illustrated in FIGS. 6-8B, there is depicted a sensor, wherein the physiological parameter is blood pressure, and where the circuitry stores data over a period of time to sense changes in blood pressure and thereby represent a physiological process. As noted, the sensor may also include a system, attached to said circuitry, to periodically receive the data, and to process the data for display on a device 160 (e.g., display 162). In addition, the collected data may be displayed for one physiological characteristic at a time or multiple characteristics may be displayed at one time. For example, display 162 in FIG. 7 illustrates temperature, blood pressure and pulse data in an exemplary representation of the top, middle and bottom portions of such a display.

In the event that device 160 were connected to sensors such as those depicted in FIG. 2, the display would depict the monitoring of the physiological parameter of respiration, where the circuitry again stores data over a period of time to sense a respiration rate and to thereby represent the physiological process of respiration.

As noted herein, the sensors 110 comprise one or a plurality of the micro-bead thermocouples, each having bead-shaped junctions wherein the physiological parameter is temperature and rate of respiration. In light of the various examples, it is apparent that various combinations of parameters may be sensed, wherein at least one sensor monitors a first physiological parameter and at least one other sensor monitors a second physiological parameter.

Per Merk (Merck Manual, 18th Edition, Copyright 2006 by Merck & Co., pp. 2549-2550), medical professionals are advised to observe the "ABCD's" for assessment in emergency situations (airway, breathing, circulation and disability). Accordingly, also contemplated in accordance with the disclosed embodiments is a signaling system, where based upon one or more of the physiological parameters being monitored, the system is able to signal (electrically, audibly or visually) medical personnel to indicate the status of the patient to whom the sensor is attached. For example, the presence or lack of sensed respiration could be signaled and to those working in a triage situation to quickly assess those injured or wounded, such information may be important. One contemplated embodiment includes a signaling component that indicates whether the specimen is respiring, and if so signals each respiration, or otherwise signals that the specimen has expired. The disclosed sensor and method may be employed to sense and monitor responses to gases, liquids, and solid acting on the bead. Hence, the sensor may be employed in a triage situation for sensing of the nasal/mouth respiration. Easily applied to multiple victims in a triage situation, the respiration sensor could quickly indicate those that are or are not breathing. The fused bead is a three-dimensional sphere and that is capable of sensing a small pressure rise or fall as a "temperature" response. Positioned in or adjacent a patient's nose, mouth or otherwise within the respiratory organs, the sensor would provide signals indicative of pressure and temperature changes.

The disclosed embodiments also contemplate the methods for sensing a physiological parameter. Such methods include the steps of (i) providing a thermocouple including a bead-shaped junction suitable for exposure to a physiological processes; (ii) exposing the bead-shaped junction to the physiological process, whereby the junction produces a signal in response to the physiological parameter; (iii) receiving the signal; (iv) converting the signal to data representing the physiological parameter; and (v) at least temporarily, storing data representing the physiological parameter. It will be appreciated that the bead-shaped (micro-bead) junction may be exposed in a non-invasive fashion or in an invasive fashion (within a flexible and temperature transmissive enclosure or envelope such as the end of a probe, catheter or the like). Preferably, the bead-shaped junction is produced in the form of a micro-bead such that said thermocouple is highly sensitive to thermo-mechanical stimuli, thereby producing a signal including a pressure component as well as temperature. In other words, the system and method would monitor a thermo-mechanical response that includes a response to change in the pressure of a gas (e.g., respiration), liquid, or even a solid. As another example of an invasive embodiment, the micro-bead sensor may be inserted into a needle, and embedded within an elastomeric material suitable for transmission of temperature and pressure so that the sensor may be used to sense, for example, internal body temperature and/or body or fluid (e.g. blood, cranial) pressure.

As noted above, one parameter that may be monitored on a specimen is temperature, where the circuitry stores temperature data over a period of time to sense changes in temperature to thereby represent the physiological process. In some embodiments, it may be important to sense and collect temperature data at a plurality of sites on the specimen and an array of sensors, spaced apart or placed at desired locations, would serve such a purpose.

In the manner of sensing respiration, using the arrangement of sensors 110 depicted in FIG. 2, the bead-shaped junction is placed in proximity to a specimen's respiratory orifice (nose, and/or mouth) to sense respiration over time, and a respiration rate is determined and output for display. The disclosed methods also contemplate placing the bead-shaped junction in proximity to an artery of a specimen to sense changes in the pressure of the artery, and where a heart rate, blood pressure and/or blood flow is determined and output. Moreover, the data collected and output may be displayed so that the user or medical personnel may review such information. The disclosed methods also contemplate interfacing to a signaling device, where signaling may be used to indicate whether the specimen is respiring, heart is pumping, etc., and if so signaling such, or otherwise signaling that the specimen has expired.

Although not specifically illustrated, it will be appreciated that additional sensors may be included with the disclosed system to provide additional feedback. For example, a senor for the orientation of the specimen (lying down, standing or sitting) may be used to correlate the physiological parameters with the specimen's orientation. Similarly, a piezoelectric sensor may be included in an array of sensors, wherein a fall or collapse of the subject may be detected. It will be appreciated that the disclosed sensor and method further contemplates the use of the various sensors in a remote configuration wherein sensor data may be periodically or continuously collected and periodically transmitted via wired or wireless transmission means to a central location for review or analysis. The local system work by the user may also include processing, monitoring and/or alarm features and functionality.

In an anticipated use situation such a cardiac stress test, the micro sensor array initial state is known when the device is turned on. The site temperature and barometric pressure become the sensor base reference. A sensor array holding device on the patient causes a counter temperature and pressure change from the skin temperature and artery pressure. A caregiver applies the sensor to the patient. Immediately before the patient is about to engage in high motion activities or be placed in a high emotion environment, the caregiver turns on the automatic monitoring function, and proceeds with his or her duties while observing the patient to ensure that the patient is quiet until the monitor acquires a certain number of waveforms without resetting. Once this has occurred, the caregiver permit the high motion activity of the specimen to begin. An automatic high motion tolerance algorithm reduces the adverse effects of high motion artifacts from the main channel using the main channel and reference channel signals.

This invention also contemplates the ability, based upon respiration, temperature and the like, to accurately characterize a specimen's caloric energy exchange or expenditure. The noninvasive measurement of a patient's blood pressure is achieved automatically in high motion situations by using a caloric sensor in a method and system that acquires pressure waveform data as thermal elastic exchange occurs during the cyclic compression and decompression of an artery varies. As described above lateral and specifically spaced micro sensor array is applied to skin surface. The interrelationship of site ambient temperature and barometric pressure acting and underlying skin area and artery pressure is profiled and the subsequent data acquired from the signals is processed to characterize he physiological parameters.

The following discussion is directed to the calibration and use of the sensing system. Assuming, for example, a 98.6° F. body temperature; a 60/40 (systolic/diastolic) blood pressure; an approximately 60 beats per minute pulse rate, and approximately 12 respirations/min respiration rate, the chart depicts the results of calculated bead expansion and contraction with and site pressure input correction for atmospheric pressure.

Consider a sensor calibration reference point or "Ice Point" at 32° F. or 0° C. The sensed temperature to such a zero reference is known as is the signal generated by the thermocouple. The pressure may then be calibrated to a known or typical pressure (example 14.7 psi). As pressure increases or decreases, the bead compression or expansion is then a programmable correction, similar to the present automated cuff system. That is how the cuff sensed site blood pressure is corrected. In a similar manner, the present sensor may be corrected or calibrated based upon the volume of the micro-bead junction. The sensor bead change in volume may be characterized as $$\text{Delta } V = \{Fb \times Db\}/\{Ab \times E\}$$

where, Fb=Force on the Bead=Pa {Atmospheric Pressure}× As {Bead surface Area $[\pi \times D^2]$}. Note that pressure correction Z=thermal mechanical flex=(e)×(E). Steel expansion is NOT constant, as e=0.000006" (micro-bead junction size)+ 0.000 000 0023×Temp actual (Ta). Hence, the Expansion rate increases as the temperature rises. And, E (Young's Modulus) is not constant, and although approximating 30,000,000 pounds per square inch at room temperature, the modulus drops with temperature rises (e.g., E=30,000,000−{(5,000,000/900)×Ta}). In other words, Temperature changes the fused bead Modulus.

AS suggested previously, the sensing system may be comparatively calibrated with a blood pressure cuff or similar means and a technician may assure correlation. Moreover, the process for conducting such a correlation test may be controlled and facilitated by a programmatic set of instructions stored in the associated workstation or handheld device 160.

Once calibrated various physiological parameters may be monitored, including but not limited to:
Respiration Temperature
 i. Inhalation ambient site source (Oxygen rich)
 ii. Exhale Internal source (Carbon Dioxide rich)
Respiration Rate
 i. Rest
 ii. Active
Body Temperature
 i. Surface
 ii. Inner tissue
Vascular Body Pressure
 i. Surface Palpitation
 ii. Inner Vascular Pulse Range
Vascular Blood Pressure Nominal
 i. Systolic High Blood flow start (60 PSI-120" Hg)
 ii. Diastolic Low Blood flow pulse fade (40 PSI-80" Hg)
Vascular Blood Flow Rate
 i. Rest
 ii. Active In accordance with the various aspects disclosed herein and in the details depicted in the exemplary embodiments of the attached figures, the disclosed sensor and method are believed suitable for monitoring one or more of the following: Temperature-Acceleration-Pressure-Pulse-Position-Sound.

The various embodiments described herein are not intended to limit the claimed invention to those embodiments described. On the contrary, the intent is to cover all alternatives, modifications, and equivalents as may be included within the spirit and scope defined by the appended claims.

It will be appreciated that various of the above-disclosed embodiments and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following or future claims.

What is claimed is:

1. A physiological sensor, comprising:
  an exposed thermocouple having a cross-wire micro-bead junction formed at the termination of two dissimilar metal wires, whereby the micro-bead junction senses a physiological parameter, said thermocouple producing a signal in response to the physiological parameter, wherein the micro-bead junction senses changes in response to thermo-mechanical stimuli and produces a signal including a pressure component where the pressure component changes in response to a fluctuation in pressure at a surface of the micro-bead junction; and
  circuitry connected to the thermocouple for receiving the signal, converting the signal to data representing at least one physiological parameter including at least the pressure component, and at least temporarily storing data representing the physiological parameter including at least the pressure component.

2. The sensor according to claim 1, wherein the physiological parameter includes body temperature, and where said circuitry also stores data over a period of time to sense changes in temperature to thereby represent a physiological process.

3. The sensor according to claim 1, wherein said thermo-mechanical stimulii include gas, liquid, or solid and where said signal includes a response to a pressure change in the gas, liquid, or solid.

4. The sensor according to claim 3, wherein said micro-bead is formed as a contact region between two dissimilar metal wires.

5. The sensor according to claim 4, wherein said contact is a welded contact.

6. The sensor according to claim 5, wherein said dissimilar metal wires have a diameter of less than 0.006 inches.

7. The sensor according to claim 6, wherein the diameter of said metal wires is no larger than 0.001 inches.

8. The sensor according to claim 1, wherein said circuitry includes a timing device and where said junction is configured to be placed in proximity to a physiological specimen's respiratory orifice to sense respiration and said circuitry outputs data including a respiration rate of the physiological specimen.

9. The sensor according to claim 1, wherein said circuitry includes a timing device and where said junction is configured to be placed in proximity to an artery of a physiological specimen to sense changes in the pressure of the artery and said circuitry outputs data including a heart rate of the physiological specimen.

10. The sensor according to claim 1, wherein said circuitry includes a pair of parallel arrays each comprising a plurality of spaced-apart junctions, and a timing device, and where said arrays of spaced-apart junctions are configured to be placed on the body of the physiological specimen in proximity to an artery of a physiological specimen and said circuitry outputs data including a flow rate of blood flowing through the artery of the physiological specimen.

11. The sensor according to claim 1, wherein the physiological parameter is blood pressure, and where said circuitry stores data over a period of time to sense changes in blood pressure and to thereby represent a physiological process.

12. The sensor according to claim 1, wherein said sensor further comprises a system to periodically receive the stored data and to process the data for presentation on a display.

13. The sensor according to claim 1, further comprising a plurality of thermocouple junctions, each having micro-bead junctions wherein the physiological parameters sensed include temperature and rate of respiration.

14. The sensor according to claim 1, further including a housing and wherein said junction is configured to be maintained in proximity to a physiological specimen by said housing.

15. A sensor, comprising:
 a welded micro-bead junction of dissimilar wires sensing both thermal and pressure stimuli, whereby the junction formed at the end of said dissimilar wires is configured to be positioned to detect pressure in the form of force applied to the physiological specimen, said junction producing a signal in response to the force; and
 circuitry connected to the junction for receiving the signal, converting the signal to data representing both thermal and pressure stimuli, and at least temporarily storing data representing the stimuli.

16. The sensor according to claim 15, wherein said signal includes a component representing an applied bead surface force.

17. A method for sensing a force at a surface of a physiological specimen, comprising:
 adapting, to the surface of the physiological specimen, a sensor including an exposed micro-bead junction of dissimilar wires sensing both thermal and pressure stimuli, whereby the junction is positioned in relation to the surface to detect the force, said junction producing a signal in response to the force, and circuitry connected to the junction for receiving the signal, converting the signal to data representing both thermal and pressure stimuli, and at least temporarily storing data representing thermal and pressure stimuli; and
 processing the data to determine, as a component of the signal, a portion of the signal due to application of the force.

18. The method of claim 17, further comprising processing the data for illustration on a display.

19. The method of claim 17 wherein said sensor includes a housing and is adapted for use with the physiological specimen by attaching the housing so that at least a surface of the sensor provides an operative connection between the physiological specimen and the micro-bead junction in order to detect the force.

* * * * *